United States Patent [19]

Davenport et al.

[11] Patent Number: 4,778,922

[45] Date of Patent: * Oct. 18, 1988

[54] PROCESS FOR PRODUCING N,O-DIACETYL-6-AMINO-2-NAPHTHOL

[75] Inventors: Kenneth G. Davenport, Corpus Christi; Charles B. Hilton, Euless, both of Tex.

[73] Assignee: Hoechst Celanese Corporation, Somerville, N.J.

[*] Notice: The portion of the term of this patent subsequent to Feb. 4, 2003 has been disclaimed.

[21] Appl. No.: 875,142

[22] Filed: Jun. 17, 1986

[51] Int. Cl.$^4$ ............................................. C07C 102/10
[52] U.S. Cl. ...................................................... 560/139
[58] Field of Search ........................................ 560/139

[56] References Cited

U.S. PATENT DOCUMENTS 4,568,763  2/1986  Davenport et al. .................. 560/42
4,593,125  6/1986  Davenport et al. ............. 568/323 X Primary Examiner—Michael L. Shippen
Attorney, Agent, or Firm—Marvin Turken; Donald R. Cassady

[57] ABSTRACT

N,O-diacetyl-6-amino-2-naphthol is produced by subjecting 2-naphthyl acetate to a Fries rearrangement or 2-naphthol and an acetylating agent to a Friedel-Crafts acetylation to form 6-hydroxy-2-acetonaphthone which is then reacted as is or as its acetate ester with hydroxylamine or a hydroxylamine salt to form 6-hydroxy-2-acetonaphthone oxime. The oxime is then subjected to a Beckmann rearrangement and accompanying acetylation with acetic anhydride to form the N,O-diacetyl-6-amino-2-naphthol.

5 Claims, No Drawings

PROCESS FOR PRODUCING N,O-DIACETYL-6-AMINO-2-NAPHTHOL

This invention relates to an integrated process for the production of N,O-diacetyl-6-amino-2-naphthol (NODAN), from 2-naphthyl acetate, or 2-naphthol and an acetylating agent as the starting material.

BACKGROUND OF THE INVENTION

Various N-acyl-acyloxy aromatic amines are known which can be used for the preparation of poly(esteramide)s capable of forming an anisotropic melt phase and suitable for being formed into shaped articles such as moldings, fibers, and films, as disclosed, for example in U.S. Pat. Nos. 4,330,457; 4,339,375; 4,341,688; 4,351,918; and 4,355,132. However, none of these patents specifically discloses NODAN for this purpose.

U.S. Pat. No. 4,568,763, issued Feb. 4, 1986 to Davenport and Hilton, discloses the production of N-acyl-acyloxy aromatic amines by forming the oxime of a hydroxy aromatic ketone and subjecting the oxime to a Beckmann rearrangement in the presence of a carboxylic acid anhydride. The patent lists 2,6-naphthylene as a contemplated aromatic group.

Davenport and Linstid, U.S. Pat. No. 4,593,125, issued June 3, 1986, teaches the acylation of 2-substituted naphthalenes, e.g., 2-naphthol, with anhydrous hydrogen fluoride as catalyst, to obtain 6-substituted-2-naphthones such as 6-hydroxy-2-acetonaphthone (6,2-HAN).

Lewis, U.S. Pat. No. 2,833,825 shows the rearrangement of esters of phenolic compounds, e.g., beta-naphthol, to hydroxyaryl alkyl ketones using anhydrous hydrogen fluoride as catalyst. The working examples of this patent are limited to the rearrangement of esters of higher fatty acids.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, show the rearrangement of phenyl acetate in hydrogen fluoride to 4-hydroxyacetophenone. They also report the same reaction carried out by K. Weichert as described in Angewandte Chemie 56, 338 (1943). In addition, Dann and Mylius disclose the formation of hydroxy aromatic ketones from rearrangements in hydrogen fluoride of m-cresyl acetate, p-cresyl acetate, and guaiacol acetate.

Dann and Mylius also disclose the reaction of phenol and glacial acetic acid in the presence of hydrogen fluoride to produce 4-hydroxyacetophenone. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone.

Muessdoerffer and Niederprum in German Offenlengungschrift No. 2,616,986, published Oct. 27, 1977, disclose the acylation of phenols and substituted phenols with an acyl chloride in the presence of hydrogen fluoride to yield the 4-acyl derivative in high yield with high selectivity. The inventors disclose that 2-naphthol and 7-chloro-2-naphthol can be acylated according to their invention but do not teach any specific method for the acylation of the naphthol derivatives nor do they indicate what isomer or isomers are produced with such naphthol derivatives.

Auwers et al, Chemische Berichte, 58, 36–51 (1925) at page 41 show the Beckmann rearrangement of a large number of oximes of aromatic ketones most of which are substituted acetophenones. However, the only attempted rearrangement of the oxime of a hydroxy aromatic ketone was that of the oxime of o-hydroxyacetophenone, but no amine was formed, i.e., the attempted rearrangement was unsuccessful; see Auwers et al at page 41.

Ganboa et al, Synthetic Communications 13, 941–944 (1983) show the production of acetanilide from acetophenone by refluxing in a solution of hydroxylamine hydrochloride. There is, however, no suggestion of the synthesis of N-acyl acyloxy aromatic amines such as NODAN.

Pearson et al; Journal of the American Chemical Society 75, 5905–5908 (1953) disclose the formation of hydrazones from ketones by reaction with hydrazine hydrate and the rearrangement of the hydrazone to the amide by reaction with sodium nitrite and concentrated sulfuric acid. Specifically, on page 5907 Pearson et al show the rearrangement of p-hydroxyacetophenone hydrazone to p-hydroxyacetanilide.

Copending application Ser. No. 870,062 filed June 3, 1986, now U.S. Pat. No. 4,675,449, by Davenport discloses the preparation of 6-hydroxy-2-acetonaphthone (6,2-HAN) by the Fries rearrangement of 2-naphthyl acetate.

SUMMARY OF THE INVENTION

In accordance with this invention, N,O-diacetyl-6-amino-2-naphthol (NODAN) is produced from 2-naphthyl acetate, or 2-naphthol and an acetylating agent such as acetic acid or anhydride, by means of an integrated process including the steps of converting the 2-naphthyl acetate, or 2-naphthol and acetylating agent, to 6-hydroxy-2-acetonaphthone (6,2-HAN) by a Fries rearrangement or Friedel-Crafts acetylation respectively, and converting the 6,2-HAN or its acetate esters, i.e., 6-acetoxy-2-acetonaphthone (6,2-AAN) to 6,2-HAN oxime with a hydroxylamine salt. The oxime is then subjected to a Beckmann rearrangement and accompanying acetylation by contacting the oxime with acetic anhydride and a Beckmann rearrangement catalyst to form NODAN.

Although the reaction of 2-naphthol and an acetylating agent is characterized herein as a "Friedel-Crafts acetylation," no opinion as to the mechanism of reaction should be implied by this characterization.

When carrying out the process of this invention using 2-naphthyl acetate as the starting material, the initial Fries rearrangement to produce 6,2-HAN from 2-naphthyl acetate is defined by equation (I):

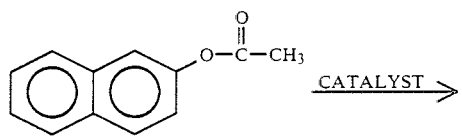 (I)

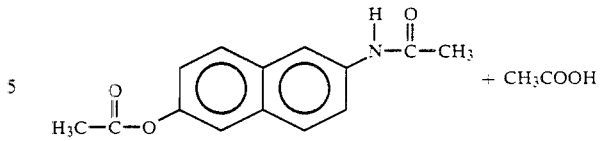

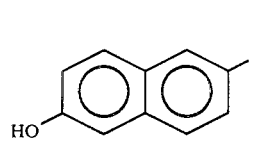

If 2-naphthol and an acetylating agent are used as the starting material, the resulting acetylation reaction to form 6,2-HAN is indicated by equation (II):

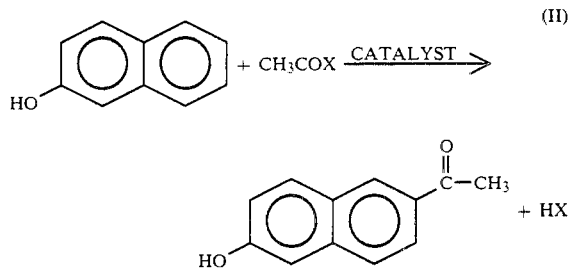 (II)

where X is the residue minus an acetyl group of compounds which are known acetylating agents. X may be, for example, hydroxy, acetoxy, or halide including fluoride, chloride, bromide, or iodide. Acetylating agents which may be used are for example, acetic anhydride, acetic acid, acetyl fluoride, acetyl chloride, and acetyl bromide.

Either 6,2-HAN or its acetate ester, i.e., 3-acetoxy-2-acetonaphthone (6,2-AAN) may be reacted with hydroxylamine to form 6,2-HAN oxime since, in the case of 6,2-AAN, the acetoxy group is hydrolyzed to hydroxy during the reaction. The oxime formation thus proceeds as in equation (III):

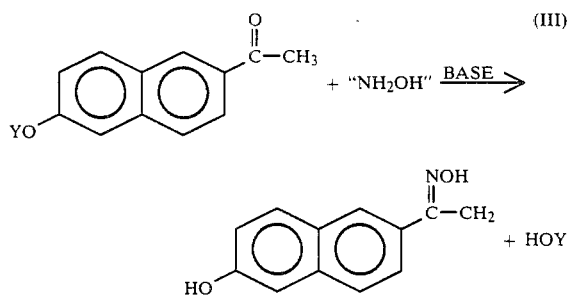 (III)

where Y is hydrogen or an acetyl group.

The Beckmann rearrangement and acetylation of 6,2-HAN oxime to form NODAN proceeds as in equation (IV):

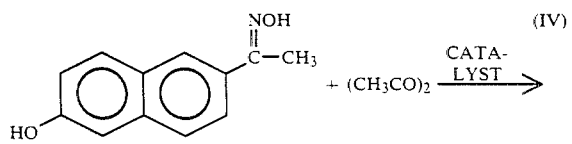 (IV)

The Fries rearrangement or Friedel-Crafts catalyst may be hydrogen fluoride or any other catalyst known in the art to be effective for the Fries or Friedel-Crafts reaction, e.g., aluminum chloride, zinc chloride, or boron trifluoride. In carrying out the reaction, the 2-naphthyl acetate, or 2-naphthol and acetylating agent, catalyst, and if desired when 2-naphthyl acetate is the starting material, an additive for the reaction for improvement of 6,2-HAN selectivity, such as acetic anhydride or acetic acid, may be charged to a corrosion-resistant reactor and the mixture maintained at a temperature, for example, of about 0° to about 100° C., preferably about 50° to 80° C. for a period, for example, of ½ to about 8 hours, preferably about ½ to 4 hours, at a pressure, for example, of about 2.5 to about 500 psig. The acetic anhydride or acetic acid additive may be used, for example in an amount of 0.1 to 2.0 moles, preferably 0.7 to 1.3 moles per mole of 2-naphthyl acetate.

If HF is used as the catalyst it may be charged as a liquid or a gas using technologies of handling well known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles, preferably, about 20 to 60 moles per mole of 2-naphthyl acetate or 2-naphthol initially present in the reaction zone. The reactants may be initially charged to the reactor, hydrogen fluoride may then be charged at a temperature less than the specified reaction temperature and the reaction adjusted to the specified reaction temperature for the specified reaction period.

If 6-acetoxy-2-acetonaphthone (6,2-AAN) is used as the starting material for the formation of 6,2-HAN oxime, it may be obtained as a co-product with the 6,2-HAN produced by the Fries rearrangement of 2-naphthyl acetate or the Friedel-Crafts acetylation of 2-naphthol, e.g., when the reaction is carried out in the presence of HF and an acid anhydride. Alternatively, it may be produced from the 6,2-HAN by reacting the latter with an acetylating agent such as acetic anhydride by contacting the 6,2-HAN with, for example, about 1 to 5 moles of the anhydride per mole of 6,2-HAN at a temperature, for example, in the range of 120° to 140° C. for a period, for example, in the range of 1 to 4 hours.

The conversion of 6,2-HAN into NODAN is accomplished by first forming the oxime from the 6,2-HAN or its acetate ester as indicated by equation (III), by contacting the 6,2-HAN or its acetate with hydroxylamine or a salt of hydroxylamine, e.g., hydroxylamine hydrochloride, hydroxylamine sulfate, hydroxylamine bisulfate, or hydroxylamine phosphate and a base, such as ammonium hydroxide, potassium hydroxide, sodium hydroxide, or lithium hydroxide in an amount, for example, of 1 to 3 moles per mole of hydroxylamine, at a temperature, for example of 0° to 60° C. for a period, for example, of 1 to 4 hours. Any pressure may be used, e.g., 80 mm of mercury to 10 atmospheres absolute. The reaction is preferably carried out in an aqueous or alcoholic medium, i.e., in the presence of water and/or an alcoholic such as methanol, ethanol, or isopropanol.

The 6,2-HAN oxime is converted into NODAN by a Beckmann rearrangement and accompanying acetylation as shown in equation (IV), by contacting the oxime with acetic anhydride and a Beckmann rearrangement catalyst at a temperature, for example of 0° to 118° C. for a period for example of 1 to 4 hours. The pressure is not critical and may be, for example, in the range of 80 mm of mercury to 10 atmospheres absolute. Any Beckmann rearrangement catalyst may be used as, for example, an acid, e.g., a mineral acid such as sulfuric, hydrochloric, or phosphoric acid, an organic acid such as trifluoroacetic acid, para-toluenesulfonic acid, benzenesulfonic acid, or methanesulfonic acid, or an acidic ion-exchange resin such as Amberlyst 15 or Nafion 501 which are sulfonic acid ion-exchange resins, or thionyl chloride in liquid sulfur dioxide. The reaction may be advantageously carried out in the presence of glacial acetic acid in an amount, for example, up to 50% by weight of the acetic anhydride. The total amount of glacial acetic acid is not critical but the total amount of anhydride or anhydride/acid mixture is such that the oxime concentration in most cases is in the range of about 2% to 50% weight at the start of the reaction.

The following examples further illustrate the invention.

DESCRIPTION OF SPECIFIC EMBODIMENTS

Example 1

This example illustrates the preparation of 6-hydroxy-2-acetonaphthone by the Fries rearrangement of 2-naphthyl acetate using hydrogen fluoride as catalyst.

To a 300 cc Hastelloy C autoclave were charged 7.0 g (0.038 mol) of 2-naphthyl acetate. The autoclave was cooled to −50° C. and evacuated to 150 mm Hg whereupon 33.3 moles of anhydrous hydrogen fluoride per mole of 2-naphthyl acetate were transferred from a cylinder to the autoclave at such a rate that the temperature did not exceed 0° C. The contents were warmed to a reaction temperature of 75° C. and stirred for 4 hours during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using a solution of 50% potassium hydroxide and the mixture was then extracted with 75 mL of ethyl acetate (3x). The organic solution was dried over anhydrous MgSO$_4$, filtered, and the solvent was removed using a rotary evaporator to yield 6-hydroxy-2-acetonaphthone.

The conversion of 2-naphthyl acetate to all products was 99.7% while the selectivity to 6,2-HAN based on all products was 67.6%, and the regioselectivity to 6,2-HAN, which is the selectivity based on the total amount of hydroxyacetonaphthone isomers produced, was >99%.

Example 2

This example illustrates the preparation of 6-hydroxy-2-acetonaphthone by the Fries rearrangement of 2-naphthyl acetate using hydrogen fluoride as catalyst with acetic anhydride as additive.

The procedure of Example 1 was followed except that one mole of acetic anhydride per mole of 2-naphthyl acetate was charged to the reactor with the latter compound, 21.3 moles of hydrogen fluoride per mole of 2-naphthyl acetate were utilized and the reaction temperature was 60° C.

The conversion of 2-naphthyl acetate was 95.2%, the selectivity to 6,2-HAN based on all products was 54.8%, the selectivity to 6,2-AAN was 20.1%, the regioselectivity to 6,2-HAN was 98.6%, and the yield of 6,2-HAN plus 6,2-AAN was 71.3%.

Example 3

This example illustrates the preparation of 6-hydroxy-2-acetonaphthone by the Friedel-Crafts acetylation of 2-naphthol with acetic acid as the acetylating agent.

A solution of 14.4 g (0.1 moles) of 2-naphthol and 24.0 g (0.2 mol) of acetic acid was cooled to −30° C. in a stainless steel autoclave. The solution was purged with 50 psig nitrogen for 15 minutes. Hydrogen fluoride, 100 g (5.0 mol), was added and the autoclave sealed.

The autoclave was rapidly heated to 80° C. and maintained at that temperature for 60 minutes. The autoclave was then rapidly cooled to 40° C. The hydrogen fluoride was purged from the autoclave at about 40° C. and then a nitrogen sweep was maintained for an additional one hour to remove the last distillable traces of hydrogen fluoride. The product was dissolved in ethyl acetate, poured onto ice, neutralized with an aqueous solution containing 45% potassium hydroxide until the aqueous solution was at about pH 6.5. The aqueous layer was re-extracted with ethyl acetate. The organic layers were combined, washed with a saturated aqueous sodium chloride solution, dried, and the solvent was removed in vacuo.

The conversion of 2-naphthol to all products was 93% while the selectivity to 6,2-HAN plus 6,2-AAN was 76%.

Example 4

This example illustrates the preparation of 6-hydroxy-2-acetonaphthone by the Friedel-Crafts acetylation of 2-naphthol with acetic anhydride as the acetylating agent.

A solution of 14.4 g (0.1 mol) of 2-naphthol and 100 g (5.0 mol) of hydrogen fluoride is prepared at −30° C. Acetic anhydride in an amount of 20.4 g (0.20 mol) was added and the reaction autoclave was sealed. The autoclave was heated rapidly to 80° C. and held at that temperature for one hour. Isolation and purification of the resulting 6-hydroxy-2-acetonaphthone and its acetate were carried out as in Example 3. The conversion of 2-naphthol to all products was 99% and the selectivity to 6,2-HAN was greater than 85%.

Example 5

This example illustrates the reaction of 6-hydroxy-2-acetonaphthone (6,2-HAN) with acetic anhydride to form 6-acetoxy-2-acetophenone (6,2-AAN).

A solution of 186.2 g (1.0 mol) of 6,2-HAN and 400 mL of acetic anhydride is heated at reflux for 3 h under a nitrogen atmosphere. The acetic acid and acetic anhydride is distilled overhead in vacuo (39°–41° C., 2.6 mm Hg). The remaining oil crystallizes upon cooling to yield 228.0 g (>99%) of white crystals indentified as 6-acetoxy-2-acetonaphthone (6,2-AAN).

Example 6

This example illustrates the formation of 6-hydroxy-2-acetonophthone (6,2-HAN) oxime from 6-acetoxy-2-acetonaphthone (6,2-AAN) and hydroxylamine sulfate.

6-Acetoxy-2-acetonaphthone (6,2-AAN, 1.18 g, 0.005 mole) and hydroxylamine sulfate (1.6 g, 0.01 mol) were dissolved in 5 ml of 10% ethanol in water. The apparatus was purged with nitrogen and then heated to 75° C. under nitrogen. Ammonium hydroxide (17M, 0.3 mL) was added with a dropper. After 30 minutes of heating at reflux, the reaction solution was cooled to 25° C., filtered and washed. The yield was 1 g after air drying.

The reaction was repeated with 0.035 mol of 6,2-AAN and a 99+% yield of 6,2-HAN oxime was again obtained.

Example 7

This example illustrates the formation of N,O-diacetyl-6-amino-2-naphthol (NODAN) by the Beckmann rearrangement and accompanying acetylation of 6,2-HAN oxime using phosphoric acid ($H_3PO_4$) and catalyst.

The oxime of 6,2-HAN was used without further purification. A reaction solution consisting of 10 g acetic acid, 5 g acetic anhydride, and 0.3 g of 85% phosphoric acid was prepared and sparged with nitrogen for 15 minutes. The oxime (0.5 g, 0.0026 mol) was added and the solution heated to reflux. After refluxing one hour the solution was cooled to 25° C. and poured into 25 mL of water. The precipitate was filtered, washed, and dried to give 0.5 g of NODAN.

The reaction was scaled up to 0.016 moles of oxime and a 88% yield was obtained.

We claim:

1. A process comprising contacting 2-naphthyl acetate with a Fries rearrangement catalyst, or 2-naphthol and a acetylating agent with a Friedel-Crafts reaction catalyst, to form 6-hydroxy-2-acetonaphthone by the Fries rearrangement of naphthyl acetate or the Friedel-Crafts acetylation of 2-naphthol respectively, contacting said 6-hydroxy-2-acetonaphthone or its acetate ester with hydroxylamine or a hydroxylamine salt and a base to form 6-hydroxy-2-acetonaphthone oxime, and containing said oxime with a Beckmann rearrangement catalyst and acetic anhydride to form N,O-diacetyl-6-amino-2-naphthol.

2. The process of claim 1 wherein hydrogen fluoride is employed as the Fries rearrangement catalyst or the Friedel-Crafts reaction catalyst.

3. The process of claim 1 wherein the Fries rearrangement of 2-naphthyl acetate is employed to produce 6-hydroxy-2-acetonaphthone as the first step in the process.

4. The process of claim 1 wherein the Friedel-Crafts acetylation of 2-naphthol with acetic anhydride is employed to produce 6-hydroxy-2-acetonaphthone.

5. The process of claim 1 wherein 6-hydroxy-2-acetonaphthone or its acetate ester is contacted with hydroxylamine phosphate to form the oxime.

* * * * *